(12) United States Patent
Masuda et al.

(10) Patent No.: US 11,246,498 B2
(45) Date of Patent: Feb. 15, 2022

(54) SENSOR, SENSOR DEVICE, AND SENSOR SYSTEM

(71) Applicant: KYOCERA Corporation, Kyoto (JP)

(72) Inventors: Yuji Masuda, Yasu (JP); Hiroyuki Mori, Yokohama (JP)

(73) Assignee: KYOCERA Corporation, Kyoto (JP)

(*) Notice: Subject to any disclaimer, the term of this patent is extended or adjusted under 35 U.S.C. 154(b) by 915 days.

(21) Appl. No.: 15/533,792

(22) PCT Filed: Dec. 16, 2015

(86) PCT No.: PCT/JP2015/006276
§ 371 (c)(1),
(2) Date: Jun. 7, 2017

(87) PCT Pub. No.: WO2016/103648
PCT Pub. Date: Jun. 30, 2016

(65) Prior Publication Data
US 2017/0332923 A1 Nov. 23, 2017

(30) Foreign Application Priority Data
Dec. 25, 2014 (JP) .............................. JP2014-262893

(51) Int. Cl.
*A61B 5/00* (2006.01)
*A61B 5/024* (2006.01)
(Continued)

(52) U.S. Cl.
CPC ........ *A61B 5/02416* (2013.01); *A61B 5/0006* (2013.01); *A61B 5/0261* (2013.01);
(Continued)

(58) Field of Classification Search
CPC .............. A61B 5/02416; A61B 5/0006; A61B 5/02427
See application file for complete search history.

(56) References Cited

U.S. PATENT DOCUMENTS 8,352,003 B2   1/2013   Sawada et al.
9,155,498 B2  10/2015   Akiyama
(Continued)

FOREIGN PATENT DOCUMENTS

JP    2002-360530 A   12/2002
JP    2007-175416 A    7/2007
(Continued)

OTHER PUBLICATIONS

International Search Report issued in PCT/JP2015/006276; dated Mar. 1, 2016.
(Continued)

*Primary Examiner* — Joseph M Santos Rodriguez
(74) *Attorney, Agent, or Firm* — Studebaker & Brackett PC

(57) ABSTRACT

A sensor includes a light emitting element, a photodetector element for receiving light emitted by the light emitting element, and a circuit board having the light emitting element and the photodetector element mounted thereon. A light emitting surface of the light emitting element is facing the circuit board which is provided with a light-transmitting portion for transmitting the light emitted by the light emitting element.

16 Claims, 12 Drawing Sheets

(51) Int. Cl.
    *A61B 5/026*     (2006.01)
    *A61B 5/0285*     (2006.01)
    *H01L 31/16*     (2006.01)

(52) U.S. Cl.
    CPC ........ *A61B 5/0285* (2013.01); *A61B 5/02427* (2013.01); *A61B 5/02438* (2013.01); *A61B 5/6824* (2013.01); *A61B 5/7214* (2013.01); *A61B 5/742* (2013.01); *H01L 31/16* (2013.01)

(56) References Cited

U.S. PATENT DOCUMENTS

| | | | |
|---|---|---|---|
| 9,167,944 B2 | 10/2015 | Akiyama | |
| 2002/0188210 A1 | 12/2002 | Aizawa | |
| 2008/0097172 A1 | 4/2008 | Sawada et al. | |
| 2011/0260176 A1* | 10/2011 | Onoe | A61B 5/0261 257/79 |
| 2012/0313208 A1* | 12/2012 | Kim | H01L 23/481 257/435 |
| 2013/0075761 A1 | 3/2013 | Akiyama | |
| 2013/0137994 A1 | 5/2013 | Sawada et al. | |
| 2014/0350366 A1* | 11/2014 | Akiyama | H01L 27/288 600/328 |
| 2014/0358012 A1* | 12/2014 | Richards | A61B 5/4812 600/479 |

FOREIGN PATENT DOCUMENTS

| | | |
|---|---|---|
| JP | 2013-073965 A | 4/2013 |
| WO | 2006/051726 A1 | 5/2006 |

OTHER PUBLICATIONS

Written Opinion issued in PCT/JP2015/006276; dated Mar. 1, 2016; with English language Concise Explanation.

* cited by examiner

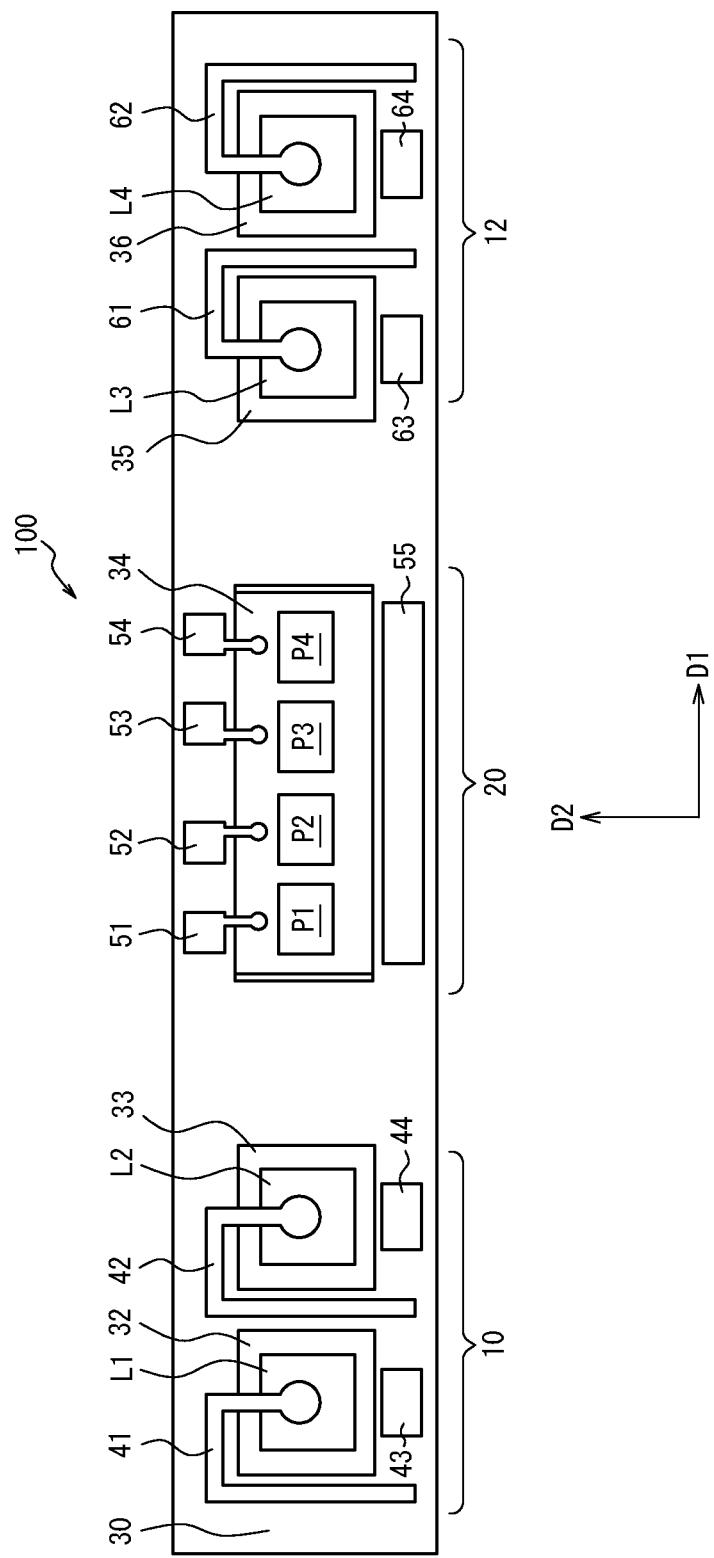

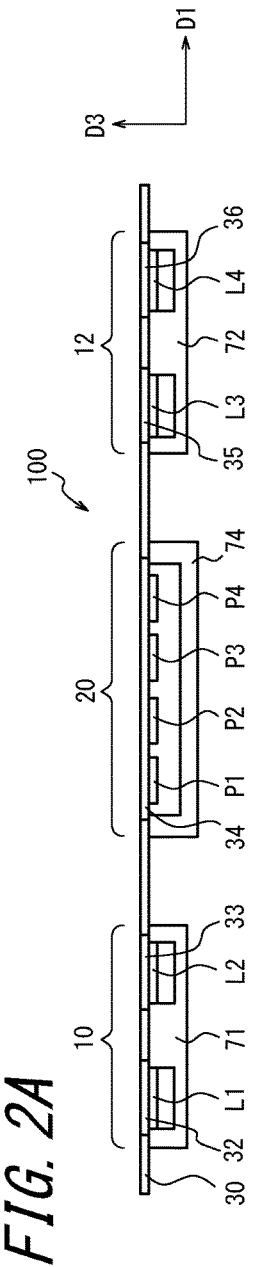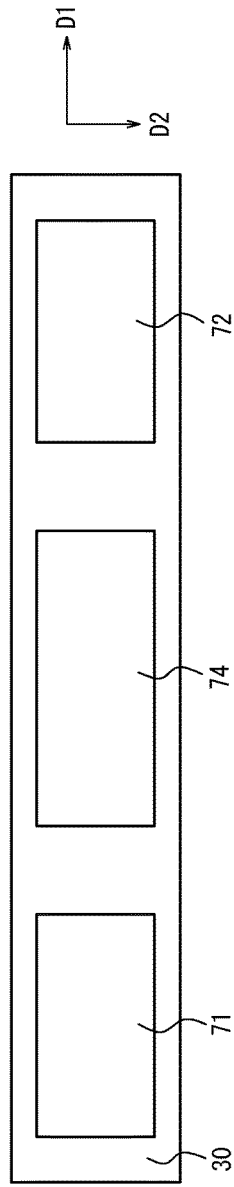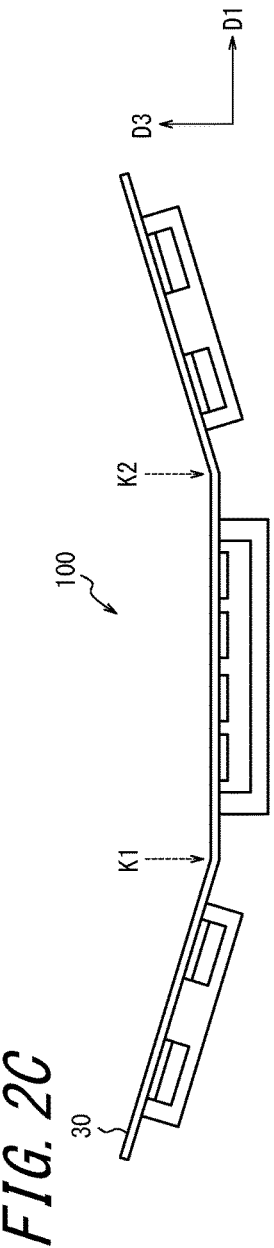

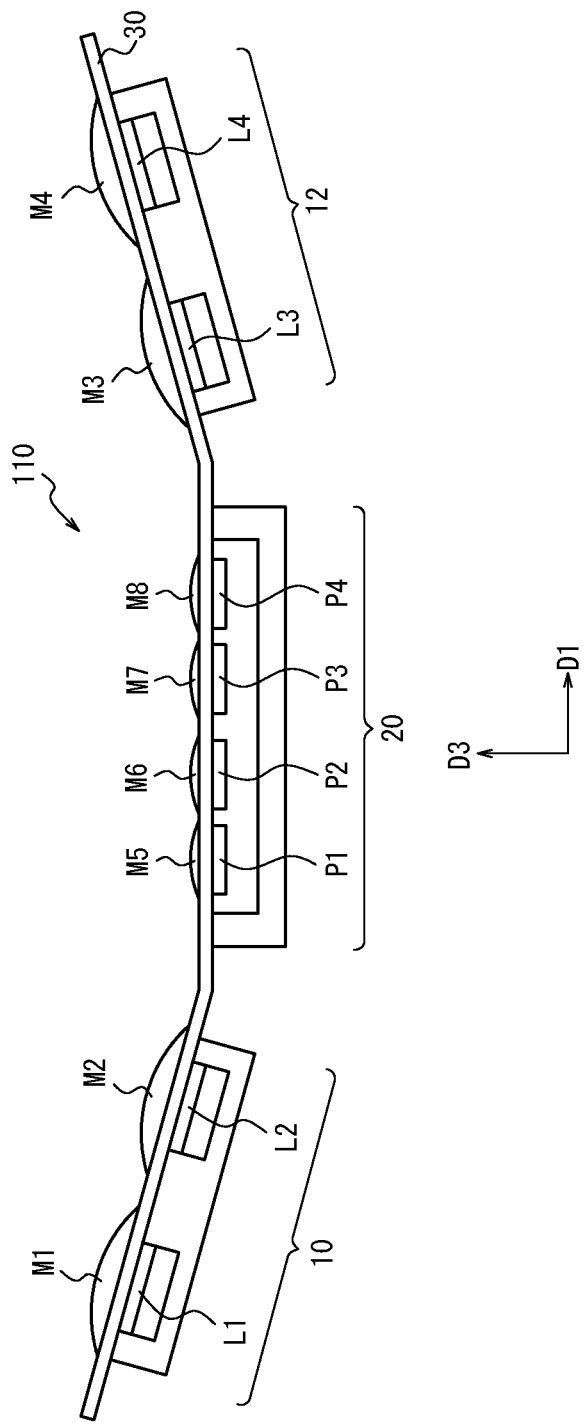

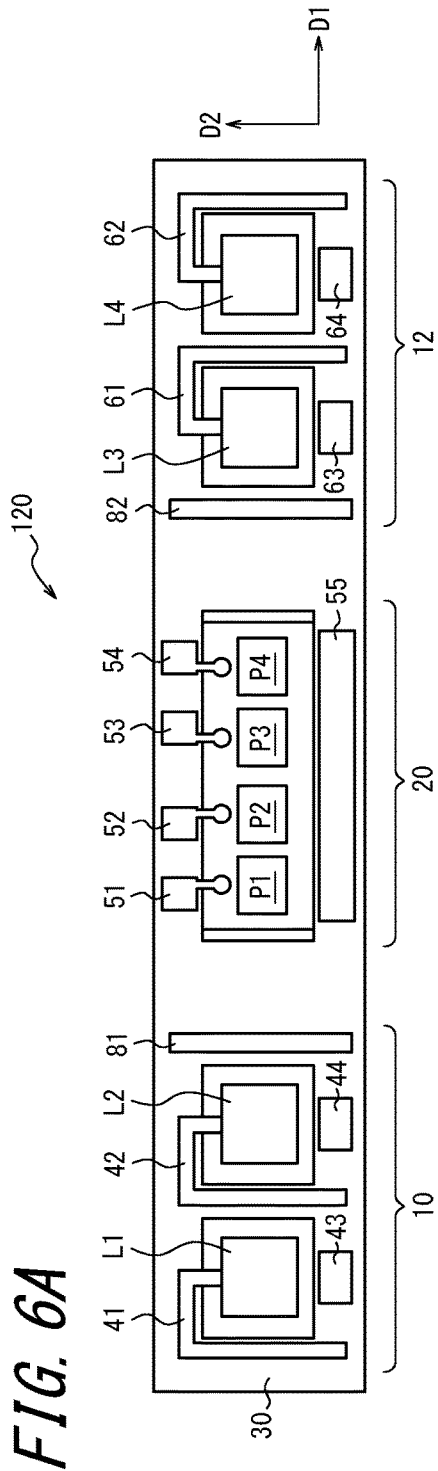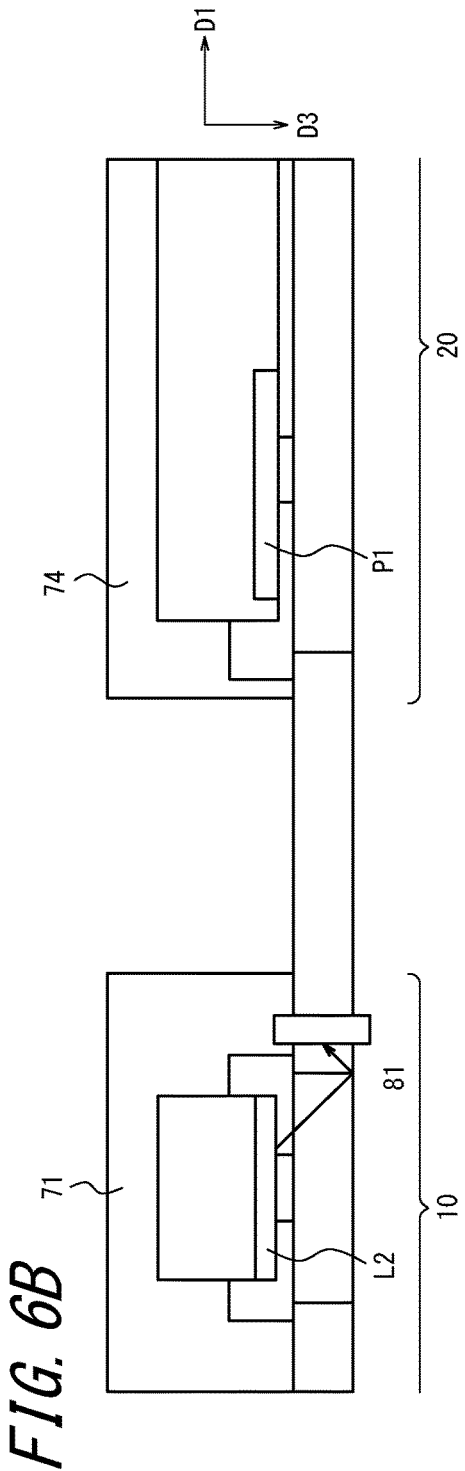

SENSOR, SENSOR DEVICE, AND SENSOR SYSTEM

CROSS REFERENCE TO RELATED APPLICATION

This application claims priority to and the benefit of Japanese Patent Application No. 2014-262893 filed on Dec. 25, 2014, the entire contents of which are incorporated herein by reference.

TECHNICAL FIELD

This disclosure relates to a sensor for measuring a pulse wave for the purpose of, for example, health management, a sensor device using the sensor, and a sensor system including the sensor device.

BACKGROUND

A heart rate representing various conditions of a human body is used as a useful indicator in various fields including health management, health enhancement, understanding a sleep state, and medical purposes. For a measurement of the heart rate, two methods have mainly been proposed: taking ECG (Electrocardiogram) from two electrodes positioned across the heart and a reference electrode, and measuring a pulse wave caused by blood flow in the blood vessel in synchronization with the heartbeat. Of these methods, taking the ECG is difficult in everyday life.

On the other hand, measuring the pulse wave is classified mainly into a reflection type and a transmission type, both of which utilize a difference between light-absorption characteristics of substances in the blood and those in other portions of the human body. For example, as the pulse wave measuring method of the reflection type, there is suggested a method as described in PLT 1 set forth below. According to this method, a light emitting element and a photodetector element arranged in parallel are placed on a surface of a living body. The light emitting element emits light into the living body, and the photodetector element detects reflected light passing through the blood vessel.

CITATION LIST

Patent Literature

PLT 1: JP-A-2002-360530

SUMMARY

Technical Problem

The pulse wave measuring method as described above is advantageous as it enables easier measurement than the ECG However, since a test site locates on the arm or leg which is moved by human activities, the pulse wave measuring method as described above also has a problem of having difficulty in stably and accurately measuring the pulse wave due to a movement of a subject person. For example, due to the movement of the subject person, a sensor containing the photodetector element and the light emitting element may be displaced, or the blood vessel may move within the body of the subject person.

Therefore, it could be helpful to provide a sensor capable of stably and accurately measuring the pulse wave, a sensor device using the sensor, and a sensor system including the sensor device.

Solution to Problem

A sensor of the disclosure includes:

a light emitting element;

a photodetector element for receiving light emitted by the light emitting element; and a circuit board having the light emitting element and the photodetector element mounted thereon, wherein a light emitting surface of the light emitting element is facing the circuit board provided with a light-transmitting portion for transmitting the light emitted by the light emitting element.

A light receiving surface of the photodetector element is facing the circuit board which may be provided with a light-transmitting portion for transmitting light to be received by the photodetector element.

The light-transmitting portion may be provided with an optical path changing element for changing at least one of an optical path of the light emitted by the light emitting element and an optical path of the light to be received by the photodetector element.

The optical path changing element may be any one of a spherical lens, an aspherical lens, a Fresnel lens, a cylindrical lens, and a prism.

The optical path changing element may be configured to direct at least a portion of the light emitted by the light emitting element toward the photodetector element.

The circuit board may comprise a resin comprising the light-transmitting portion.

The circuit board may include a portion for shielding the light emitted by the light emitting element.

The circuit board and the optical path changing element may be integrally formed.

The light emitting element may be configured with a plurality of light emitting elements linearly arranged.

The photodetector element may be configured with a plurality of photodetector elements linearly arranged.

The light emitting elements may be arranged on both sides of the photodetector element.

A sensor device of the disclosure includes:

a light emitting element for emitting light to a test site;

a photodetector element for receiving at least one of reflection light and scattered light from the test site; and a circuit board having at least one of the light emitting element and the photodetector element mounted thereon, wherein a light emitting surface of the light emitting element is facing the circuit board.

A sensor system of the disclosure includes:

a sensor device including a light emitting element for emitting light to a test site, a photodetector element for receiving at least one of reflection light and scattered light from the test site, and a circuit board having at least one of the light emitting element and the photodetector element mounted thereon, wherein a light emitting surface of the light emitting element is facing the circuit board; and a display apparatus for displaying bio-information based on a sensor signal acquired by the sensor device.

Advantageous Effect

According to the sensor, the sensor apparatus using the sensor, and the sensor system of the disclosure, the pulse wave may be measured stably and accurately.

BRIEF DESCRIPTION OF THE DRAWINGS

In the accompanying drawings:

FIG. 1 is a top view illustrating a schematic configuration of a sensor according to an embodiment;

FIGS. 2A and 2C are cross-sectional side views illustrating the schematic configuration of the sensor according to the embodiment, and FIG. 2B is a bottom view illustrating the schematic configuration of the sensor according to the embodiment;

FIG. 5 is a cross-sectional side view illustrating a schematic configuration of a sensor of another embodiment;

FIG. 6A and FIG. 6B are a top view and a cross-sectional side view, respectively, both of which are illustrating a schematic configuration of a sensor of still another embodiment;

DETAILED DESCRIPTION

Figure 3:
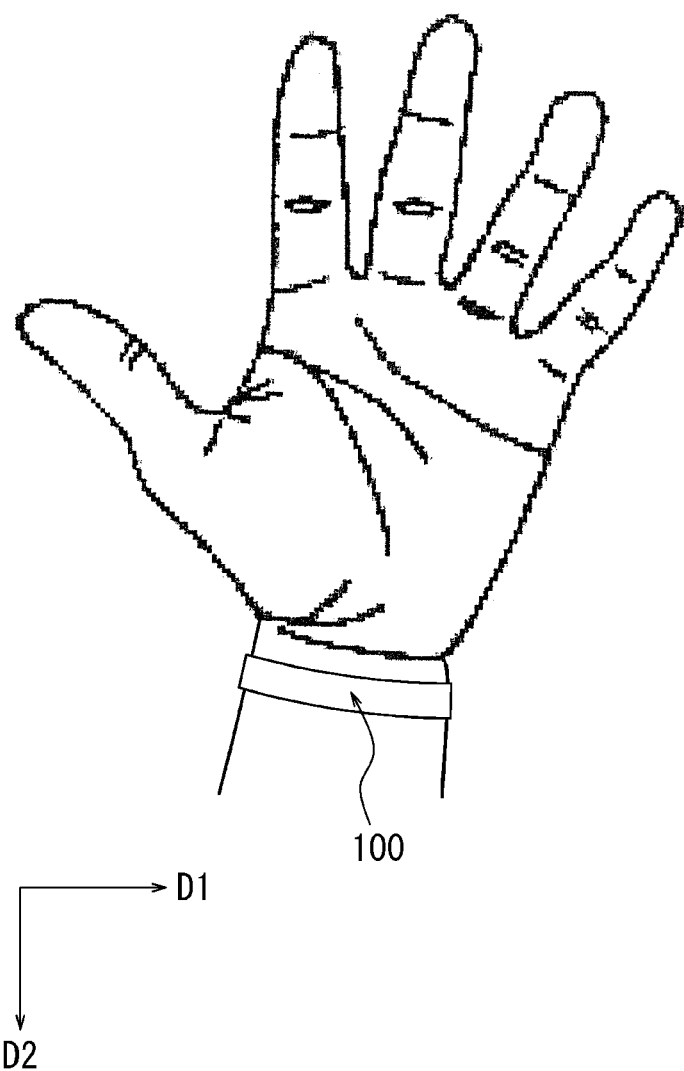
FIG. 3 is a schematic diagram illustrating an example in which a pulse wave sensor implementing the sensor of the embodiment is worn on a human body.

Hereinafter, embodiments of the disclosure will be described in detail with reference to the accompanying drawings. It is to be understood that the following description is presented for the purpose of describing the embodiments of the disclosure by way of example and should not be construed as limiting in scope.

Sensor 100

FIG. 1 is a top view illustrating a schematic configuration of a sensor of an embodiment. In FIG. 1, a horizontal direction is referred to as a first direction D1 in which a rightward direction is a positive direction thereof, and a vertical direction is referred to as a second direction D2 in which an upward direction is a positive direction thereof. In FIG. 1, that is, a top view of the sensor of the present embodiment is illustrated in a D1-D2 plane. In FIG. 1, also, a direction orthogonal to the first direction D1 and the second direction D2 is referred to as a third direction D3. The third direction D3 includes a positive direction directed to a viewer of the figure from the figure and an opposite direction (a negative direction) directed backward from the figure. That is, FIG. 1 is a diagram of the sensor of the present embodiment viewed in a direction from the positive direction of the third direction D3 to the negative direction of the third direction D3.

A sensor 100 emits light to a surface of a living body of a subject, receives the light having traveling through the living body and reaching a photodetector element, and acquires a pulse wave signal indicative of a change in a blood flow. In an example described below, the sensor 100 is placed on an inner wrist to measure the ulnar artery or the radial artery.

As illustrated in FIG. 1, the sensor 100 includes light emitting element units 10 and 12 and a photodetector element unit 20.

The light emitting element units 10 and 12 include a plurality of light emitting elements L arranged along the first direction DE In an example illustrated in FIG. 1, the light emitting element unit 10 includes two light emitting elements L1 and L2 disposed on a circuit board 30 with a predetermined gap therebetween. According to the present embodiment, the circuit board 30 is configured with any flexible substrate (flexible print substrate) that is flexible and deformable. Such a flexible substrate may be formed of, for example, a resin such as polyimide and PET. In the example illustrated in FIG. 1, also, the light emitting element unit 12 includes two light emitting elements L3 and L4 disposed on the circuit board 30 with a predetermined gap therebetween. According to the present embodiment, the light emitting element L may be configured with any light emitting element such as a light emitting diode and a laser diode. The light emitting element L emits any one of green light (wavelength of 500 to 550 nm), red light (wavelength of 630 to 780 nm), and near-infrared light (wavelength of 800 to 1600 nm). Or, the light emitting elements L1 to L4 may emit light with different wavelengths. Since the light having a long wavelength may reach a deeper position inside the body before attenuating as compared to the light having a short wavelength, using the light emitting element for emitting the near-infrared light possibly improves measurement accuracy.

The photodetector element unit 20 includes a plurality of photodetector elements P arranged along the first direction D1. In the example illustrated in FIG. 1, the photodetector element unit 20 includes four photodetector elements P1 to P4 arranged at predetermined intervals on the circuit board 30. According to the present embodiment, as described above, the light emitting element L may be configured with a plurality of light emitting elements (e.g., L1 and L2 or L3 and L4) linearly arranged. Similarly, the photodetector element P may be configured with a plurality of photodetector elements (e.g., P1 to P4) linearly arranged. In the present embodiment, the photodetector element P may be configured with any photodetector element such as a photodiode and phototransistor. The photodetector element P has sensitivity characteristics corresponding to the wavelength of the light emitted by the light emitting element L. The sensor 100 of the present embodiment, as described above, includes the light emitting elements L, the photodetector elements P for receiving the light emitted by the light emitting elements L, and the circuit board 30 having the light emitting element L and the photodetector element P mounted thereon.

On the circuit board 30, as illustrated in FIG. 1, the light emitting elements L1 and L2 of the light emitting element unit 10, the light emitting elements L3 and L4 of the light emitting element unit 12, and the photodetector elements P1 to P4 of the photodetector element unit 20 are linearly arranged along the first direction D1. However, the sensor 100 may have a different structure depending on a measurement subject. For example, at least some of the light emitting element unit 10, the light emitting element unit 12, and the photodetector element unit 20 may be arranged in a plurality of rows, e.g., two rows in parallel with the first direction D1. In this case, for example, two of the light emitting element units 10 and 12 and the photodetector element unit 20 may be arranged having longitudinal directions thereof along the first direction D1 and, simultaneously, being spaced apart from each other by a predetermined distance, e.g., 15 mm in the second direction D2. In this arrangement, the light emitting elements L and the photodetector elements P may be positioned substantially perpendicular to the ulnar artery in the wrist of the subject such that measurement is taken place at two positions spaced apart from each other by the predetermined distance, e.g., 15 mm.

In the present embodiment, respective distances between centers of the plurality of light emitting elements L and respective distances between centers of the plurality of photodetector elements P are identical to one another.

In the present embodiment, distances between the centers of the plurality of (i.e., intervals of) the photodetector elements P1 to P4, a distance between the light emitting element L1 and the light emitting element L2, and a distance between the light emitting element L3 and the light emitting element L4 are all between 0.5 mm and 1 mm. Also, distances between the light emitting element unit 10 and the photodetector element unit 20 and between the light emitting element unit 12 and the photodetector element unit 20 are between 2 mm and 3 mm. Further, each of the photodetector elements P1 to P4 has a size smaller than the distance therebetween in the first direction D1 and between 0.2 mm and 0.5 mm in the second direction D2. Each of the light emitting elements L1 to L4 has a 0.3 mm square shape.

In the present embodiment, on the circuit board 30 illustrated in FIG. 1, the light emitting element L is disposed with a light emitting surface thereof directed in the positive direction of the third direction D3 (the direction directed forward from the figure), i.e., disposed in what is called a face-down state. In FIG. 1, the light emitting element L is arranged on a rear surface of the circuit board 30 having the light emitting surface thereof facing the rear surface of the circuit board 30. Similarly, the photodetector element P may be disposed with a light receiving surface directed in the positive direction of the third direction D3, i.e., disposed in the face-down state. In other words, in the sensor 100 at least the light emitting surface of the light emitting element L is facing the circuit board 30. In the sensor 100, also, the light receiving surface of the photodetector element P may also be facing the circuit board 30.

As illustrated in FIG. 1, also, the circuit board 30 includes light-transmitting portions 32, 33, 35, and 36 which are formed of, for example, a light-transmitting material for transmitting the light emitted by the light emitting elements L1, L2, L3, and L4 disposed in the face-down state. The circuit board may further include a light-transmitting portion 34 formed of, for example, the light-transmitting material such that the photodetector elements P1 to P4 disposed in the face-down state receive, through the light-transmitting portion 34, the light emitted by the light emitting element L. Although in FIG. 1 the light-transmitting portion 34 is one element for transmitting the light heading to the photodetector elements P1 to P4 altogether, four light-transmitting portion 34 respectively corresponding to the photodetector elements P1 to P4 may be provided. In the sensor 100 of the present embodiment, as described above, the circuit board 30 includes the light-transmitting portion for transmitting the light emitted by the light emitting element L. The sensor 100 may also include the light-transmitting portion for transmitting the light to be received by the photodetector element P. According to the present embodiment, as described above, the circuit board 30 may be formed of a resin (the flexible substrate) having the light-transmitting portions.

According to the present embodiment, as illustrated in FIG. 1, electrodes 41, 42, 51 to 54, 61, and 62 for flip chip bonding are formed on the light-transmitting portions 32 to 36. According to the present embodiment, further, beside the light-transmitting portions 32 to 36, electrodes 43, 44, 55, 63, and 64 are formed for wire-bonding from the rear surface of the circuit board 30. According to the present embodiment, therefore, at least a first electrode is provided on the light-transmitting portion of the circuit board 30 configured with the flexible substrate.

FIG. 2 are diagrams illustrating the sensor 100 of FIG. 1 viewed from different viewpoints. FIG. 2A is a cross-sectional view illustrating the sensor 100 of FIG. 1 cut along a D1-D3 plane. FIG. 2B is a diagram illustrating the sensor 100 of FIG. 1 viewed in a direction directed from the negative direction of the third direction D3 to the positive direction, i.e., FIG. 2B is a rear view of the sensor 100 of FIG. 1.

As illustrated in FIG. 2A, the light emitting element unit 10 configured with the light emitting elements L1 and L2 is accommodated in a housing 71 on the rear surface of the circuit board 30. Similarly, the light emitting element unit 12 configured with the light emitting elements L3 and L4 is accommodated in a housing 72 on the rear surface of the circuit board 30. Further, the photodetector element unit 20 configured with the photodetector elements P1 to P4 is accommodated in a housing 74 on the rear surface of the circuit board 30. The housings 71, 72, and 74 may be respectively sealed with a non-light-transmitting resin on the rear surface of the circuit board 30. In FIG. 2A, the electrodes 41 to 44, members 51 to 55, and members 61 to 64 are omitted.

As illustrated in FIG. 2B, the light emitting element unit 10, the light emitting element unit 12, and the photodetector element unit 20 are respectively protected by the housing 71, the housing 72, and the housing 74, on the rear side of the circuit board 30. Also, when these housings are formed of non-light-transmitting resin or the like, the light emitted by the light emitting element L is prevented from leaking from the rear side of the circuit board 30.

FIG. 2C is a diagram illustrating an effect of the sensor 100 according to the present embodiment.

FIG. 2C is a diagram illustrating a state in which the sensor 100 of FIG. 2A is bent. As illustrated in FIG. 2C, the sensor 100, when the circuit board 30 is formed of a deformable material such as the flexible substrate, may be bent at positions K1 and K2 as illustrated in the figure. At this time, the sensor 100 may be bent in such a manner that, while a portion of the sensor 100 having the photodetector element unit 20 mounted thereon is fixed, portions of the sensor 100 having the light emitting element units 10 and 12 mounted thereon are moved in the positive direction of the third direction D3. The sensor 100 of the present embodiment, as described above, has the light emitting elements and the photodetector elements mounted on an outer side of a curve of the flexible material (i.e., on the rear surface of the circuit board 30). When the sensor 100 has a structure in this manner, a subject measured by the sensor 100 is located inside the curve (i.e., on a front surface of the circuit board 30). Therefore, portions of the flexible substrate having the light emitting elements and the photodetector elements mounted thereon are formed to be transmitting, and these elements are mounted by employing the flip chip bonding.

FIG. 3 is a schematic diagram illustrating an example in which the sensor 100 of the present embodiment functioning as a pulse wave sensor is worn on a human body.

As illustrated in FIG. 3, the sensor 100 is worn with detection units facing a palm side of the wrist such that at least one of the light from the light emitting elements L1 and L2 and the light from the light emitting elements L3 and L4 is emitted to the human body. In the example of the figure, the sensor 100 is worn on the wrist with the light emitting elements L1 and L2, the photodetector elements P1 to P4, and the light emitting elements L3 and L4 arranged across the ulnar artery close to the pinky. In this example, the ulnar artery runs substantially parallel to the second direction D2. Or, the sensor 100 may be worn on the wrist having a similar positional relationship with the radial artery close to the thumb, in place of the ulnar artery. As illustrated in FIG. 3, when the sensor 100 of the present embodiment is substantialized by the flexible substrate, the sensor 100 may bend along a particular curve of the wrist of the subject.

Figure 4A:
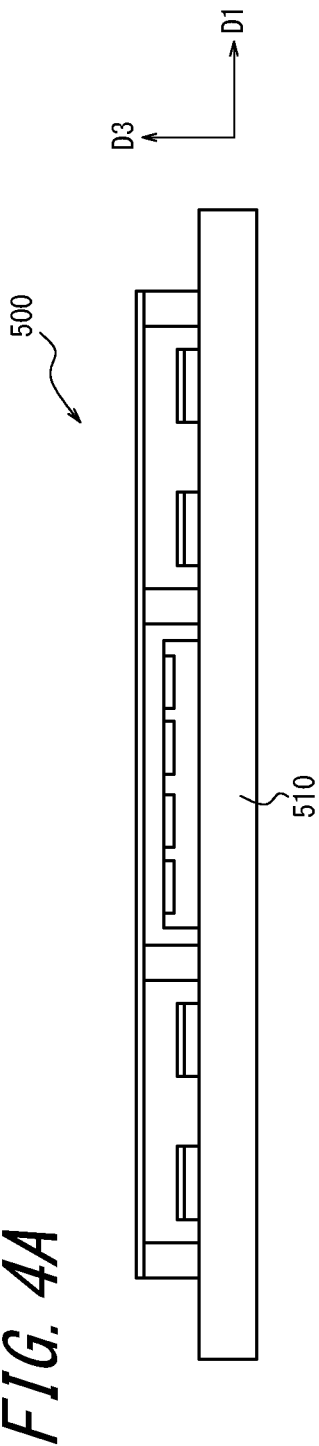
FIGS. 4A and 4B are cross-sectional side views illustrating a schematic configuration of a conventionally assumed sensor.
Figure 4B:
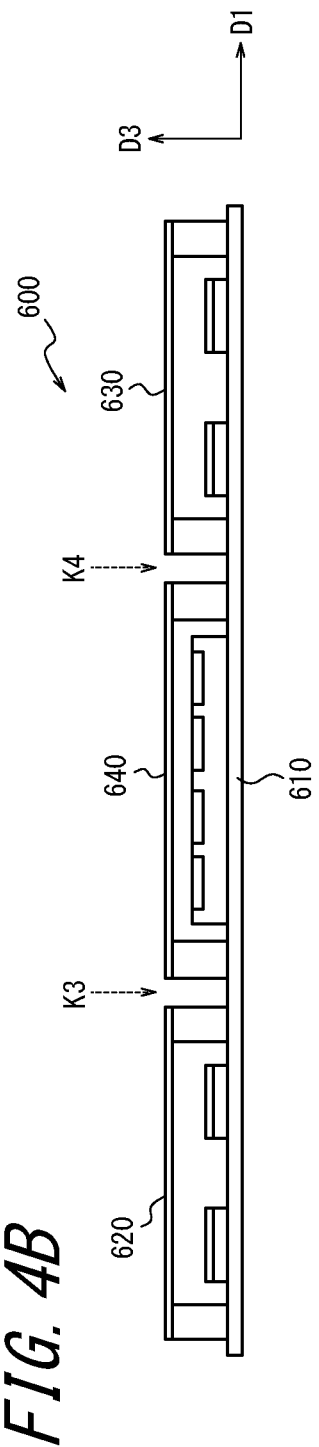

FIGS. 4A and 4B are cross-sectional side views illustrating a schematic configuration of a conventionally assumed sensor. The following is a description of advantages of the sensor 100 of the present embodiment as compared to the conventionally assumed sensor illustrated in FIGS. 4A and 4B.

A conventional sensor 500 illustrated in FIG. 4A includes a PCB substrate 510 which is non-deformable and having light emitting elements and photodetector elements mounted thereon. As illustrated in FIG. 4A, using the PCB substrate makes the light emitting elements L and the photodetector elements P enclosed together, hindering the bending of the sensor along the curve of the subject's arm. Therefore, the light emitting elements and the photodetector elements mounted on the PCB substrate cannot follow the particular curve of the wrist and have a gap from the living body. Having the gap from the living body, the conventional sensor 500 has a difficulty in measuring the pulse wave in a stable and accurate manner. Also, when the light emitting elements L at both ends are in tight contact with the living body, the photodetector element P located between the light emitting elements L is strongly pressed against the living body, affecting the blood flow and inhibiting the accurate measurement of the pulse wave. As can be seen from FIG. 4A, in order to make the PCB substrate 510 bendable, at least separate enclosure of the light emitting element L and the photodetector element P is necessary.

A conventional sensor 600 illustrated in FIG. 4B includes a flexible substrate 610 having light emitting elements L and photodetector elements P mounted on a front surface thereof, i.e., mounted in a face-up manner. Since the light emitting elements L and the photodetector elements P are mounted on the flexible substrate, a portion of the conventional sensor 600 having these elements mounted thereon illustrated in FIG. 4B may be bent. However, in order to protect a bonding wire by, for example, coating the bonding wire with a transparent resin, housings such as the housings 71, 72, and 74 of the sensor 100 of the present embodiment are necessitated. That is, in order to have the conventional sensor 600 with the bonding wire protected by the resin, the housings need to be provided at three positions in a light-sealing manner. In this case, in order to allow the flexible substrate 610 to bend at positions K3 or K4 illustrated in FIG. 4B, housings 620, 630, and 640 need to be spaced apart from each other. However, too much space between the light emitting elements L and the photodetector elements P lowers the intensity of the light received by the photodetector elements P, making it difficult to accurately measure the pulse wave.

Also, when the light emitting element and the photodetector element are mounted on a surface of the flexible substrate facing the living body as described above, a chip-on-board technology may not be employed. Therefore, due to the necessity for packaging, an increase in the number of assemblies is inevitable. That is, when the light emitting element and the photodetector element are mounted in the face-up manner by employing the chip-on-board technology, housings for protection of the bonding wire and a chip are required.

On the other hand, the sensor 100 of the present embodiment employs the face-down state of the light emitting elements and the photodetector elements on the light-transmitting portion of the flexible substrate. Therefore, when the wire bonding is employed, the light emitting elements and the photodetector elements may be sealed by resin-coating of the wire alone. Also, since the necessity for packaging optical semiconductors of the light emitting elements and the photodetector elements is eliminated, the number of assemblies may be reduced. Also, the light emitting elements L and the photodetector elements P may follow the particular curve of the wrist and, when the light emitting elements L and the photodetector elements P may come into tight contact with the wrist, a pulse wave velocity may be measured accurately without application of an extra pressure. Further, since the light is emitted from the rear side of the flexible substrate, a lens may be provided in a portion of the flexible substrate for the purpose of appropriately changing an optical path of the light.

Sensor 110

Next, a sensor according to another embodiment will be described.

FIG. 5 is a cross-sectional side view illustrating a schematic configuration of the sensor of the another embodiment. The following is a description of a sensor 110 according to the another embodiment.

As illustrated in FIG. 5, the sensor 110 includes lenses M1 to M8 provided on a surface of the flexible substrate, i.e., a surface of the circuit board 30 opposite to the surface having the light emitting elements L and the photodetector elements P mounted thereon. In this example, on the circuit board 30 the lenses M1 and M2 are provided in a manner respectively corresponding to the light emitting elements L1 and L2 constituting the light emitting element unit 10. Also, the lenses M3 and M4 are provided in a manner respectively corresponding to the light emitting elements L3 and L4 constituting the light emitting element unit 12. Further, the lenses M5 to M8 are provided in a manner respectively corresponding to the photodetector elements P1 to P4 constituting the photodetector element unit 20. That is, when the circuit board 30 is provided with lenses, the lenses are preferably provided to the light-transmitting portions 32 to 36.

When the lens is provided to the light-transmitting portion on the surface of the flexible substrate opposite to the surface having the light emitting elements L and the photodetector elements P mounted thereon, the lens may be either an aspherical lens or a Fresnel lens and does not require adjustment of the focus. In the another embodiment, therefore, highly accurate positioning of the lens is not necessary. In the another embodiment, further, various structures may be provided such as a structure in which the Fresnel lenses integrally formed with the light emitting element or the photodetector element and having a sheet-like shape are attached together, or a structure in which a cylindrical lens is used.

In the another embodiment, by providing the lenses M to the light-transmitting portions 32 to 36 of the circuit board 30, an optical path of the light emitted by the light emitting element L or an optical path of the light to be received by the photodetector element P may be changed or concentrated. When the lens M is provided to the light-transmitting portion of the flexible substrate having the light emitting element L mounted thereon, the light may be concentrated on a measurement target, e.g., the ulnar artery. Further, when the lens is provided to the light-transmitting portion of the flexible substrate having the photodetector element P mounted thereon, more light may be concentrated and received. In the another embodiment, as described above, the light-transmitting portion 32 may be provided with an optical path changing element such as the lens M for changing at least one of the optical path of the light emitted by the light emitting element L and the optical path of the light to be received by the photodetector element P. Also, the optical path changing element may have a function to reflect the light in addition to the function to concentrate the light. The optical path changing element may be any one of the spherical lens, the aspherical lens, the Fresnel lens, the cylindrical lens, and the prism. The optical path changing element and the circuit board 30 may be separately formed and attached together, or integrally formed. Further, the optical path changing element may be configured to direct at least a portion of the light emitted by the light emitting element L toward the photodetector element P.

Sensor 120

Next, a sensor according to still another embodiment will be described.

FIGS. 6A and 6B are diagrams illustrating a schematic configuration of the sensor of the still another embodiment.

FIG. 6A is a top view of the sensor of the still another embodiment, and FIG. 6B is a cross-sectional side view enlarging a portion of a sensor 120. The following is a description of the sensor 120 of the still another embodiment.

As illustrated in FIG. 6A, the sensor 120 includes a through-electrode 81 between the light emitting element unit 10 and the photodetector element unit 20. Also, the sensor 120 includes a through-electrode 82 between the photodetector element unit 20 and the light emitting element unit 12. In this way, the sensor 120 of the still another embodiment includes the through-electrodes 81 and 82 formed through the flexible substrate, i.e., the circuit board 30 between the light emitting element unit 10 and the photodetector element unit 20 and between the light emitting element unit 12 and the photodetector element unit 20. As illustrated in FIG. 6B, the through-electrodes 81 and 82 shield the light traveling through the flexible substrate. Accordingly, the light emitted by the emitting element L may be prevented from being received by the photodetector element P without passing through a surface of the living body of the subject.

In the sensor 120 of the still another embodiment, the through-electrodes 81 and 82 of the circuit board 30 simply need to include a portion for shielding the light emitted by the light emitting element L. The portion for shielding the light emitted by the light emitting element L may be formed of, for example, a black resin.

Implementation of Elements in Sensor 100

Figure 7A:
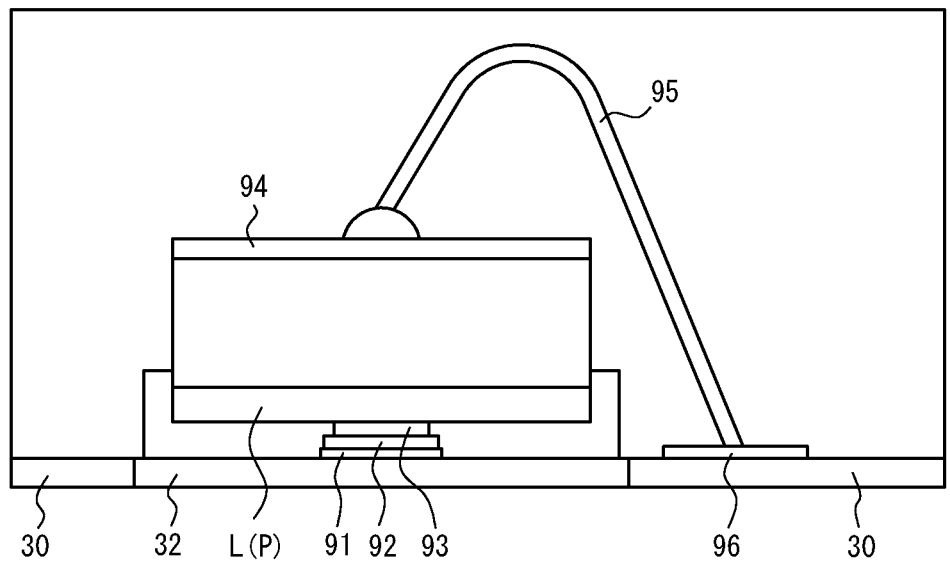
FIGS. 7A and 7B are cross-sectional side views illustrating a mounting structure of the sensor of the embodiment.
Figure 7B:
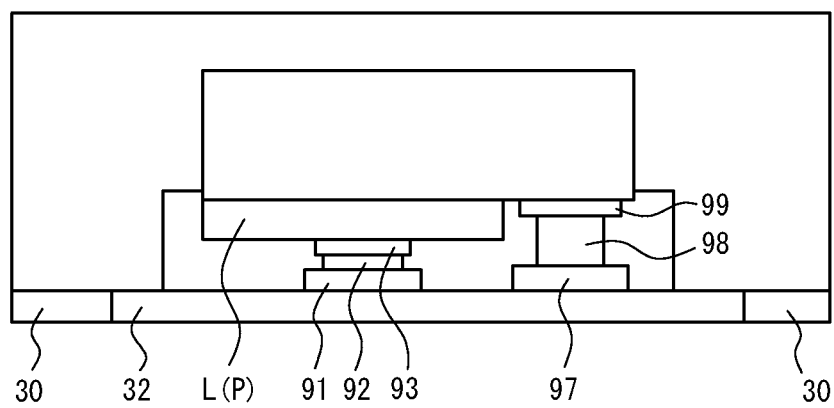

Next, implementation of a semiconductor element in the sensor of the present embodiment will be described. FIGS. 7A and 7B are diagrams illustrating schematic configurations of the implementation of the semiconductor element in the sensor of the present embodiment.

FIG. 7A illustrates an example in which one of an electrode of the light emitting element L and an electrode of the photodetector element P is mounted by employing the flip chip bonding. In FIG. 7A, an electrode 91 and an electrode 93 are joined together via a solder 92. An electrode 94 is connected to an electrode 96 for wire bonding provided in the vicinity of the light-transmitting portion 32 via a wire 95.

FIG. 7B illustrates an example in which both electrodes of the light emitting element L or the photodetector element P are mounted by employing the flip chip bonding. In FIG. 7B, the electrode 91 and the electrode 93 are joined together via the solder 92, and the electrode 97 and the electrode 99 are joined together via a solder 98.

Between the light emitting element L or the photodetector element P and the flexible substrate, i.e., the circuit board 30, a resin material with a refractive index similar to that of the light-transmitting portion of the flexible substrate may be inserted. Thereby, the light emitting element unit configured with the light emitting element L or the photodetector element unit configured with the photodetector element P may be electrically protected. In this case, connection without employing the wire bonding may reduce an amount of resin inserted.

In the sensor 110 of the present embodiment, bare-chip mounting may be employed to mount the photodetector element or the light emitting element. In this case, the photodetector element or the light emitting element is fitted on the circuit board 30 by employing wire bonding from a rear side thereof and enclosed in the light-sealing manner by a transparent resin coated on a mounting surface. In this case, also in the vicinity of the photodetector element or the light emitting element, a non-light-transmitting resin may be coated for the purpose of light sealing. On the surface of the circuit board 30 opposite to the surface having the photodetector element and the light emitting element mounted thereon, a sheet-like Fresnel lens may be disposed. The light-transmitting portion of the flexible substrate may have the optical path changing element such as the Fresnel lens integrally formed therewith.

Measurement Principle of Sensor 100

Next, a pulse wave measuring mechanism of the sensor 100 according to the present embodiment will be described.

Figure 8A:
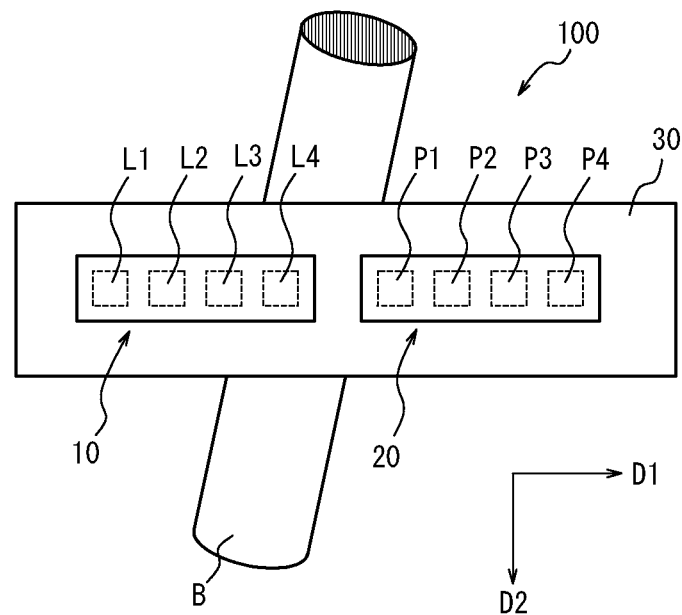
FIGS. 8A and 8B are diagrams illustrating a positional relationship between a blood vessel and the sensor of the embodiment.
Figure 8B:
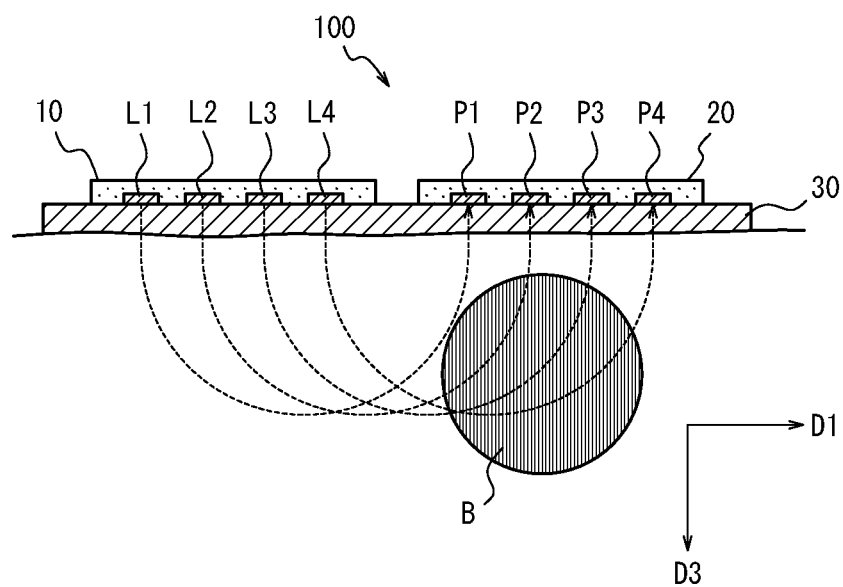

FIGS. 8A and 8B are diagrams illustrating a positional relationship between the sensor 100 and the blood vessel when the sensor 100 is worn on the human body as illustrated in FIG. 3. For simplicity of explanation, hereinafter, the sensor 100 of the present embodiment includes the light emitting element unit 10 configured with the light emitting elements L1 to L4 and the photodetector element unit 20 configured with the photodetector elements P1 to P4. Note that the sensor 100 having the light emitting element units 10 and 12 and the photodetector element unit 20 as illustrated in FIG. 1 may measure the pulse wave by employing a similar mechanism.

FIG. 8A is a top view illustrating a positional relationship between the sensor 100 and a blood vessel B. FIG. 8B is a cross-sectional view of the sensor 100 and the blood vessel B illustrated in FIG. 8A taken from the D1-D3 plane. FIG. 8A illustrates a state in which the sensor 100 is worn with a surface opposite to the surface having the light emitting element unit 10 and the photodetector element unit 20 mounted thereon (the light emitting surface of the light emitting element L) facing the blood vessel B (the skin). FIG. 8A is a diagram viewed from the surface of the sensor 100 having the light emitting element unit 10 and the photodetector element unit 20 mounted thereon. In FIG. 8A, therefore, the light emitting elements L in the light emitting element unit 10 and the photodetector elements L in the photodetector element unit 20 are indicated by broken lines.

As illustrated in FIG. 8A, the sensor 100 is disposed in such a manner that the first direction D1 crosses an extending direction of the blood vessel B. The sensor 100 is disposed in such a manner that the first direction D1 and the blood vessel B preferably form an angle of 60 degrees to 90 degrees therebetween, or more preferably become substantially perpendicular to each other.

Thereby, when the light emitting elements L1 to L4 are lit up, the light emitted therefrom is irradiated to the human body, travels through the human body, and then received by the photodetector elements P1 to P4. Each of the photodetector elements P1 to P4 receives the light having traveled through the human body and thus having intensity reflecting substances in a traveling path. Analysis of a detection signal associated with the intensity of the light received by the photodetector elements P1 to P4 provides the pulse wave signal corresponding to a change in a diameter of the blood vessel caused by extension and contraction of the blood vessel.

The sensor 100 configured in this manner may obtain the pulse wave signal accurately and stably even when a relative position between the blood vessel B and the sensor 100 changes. The following is a detailed description of such a mechanism with reference to FIGS. 9A and 9B.

Figure 9A:
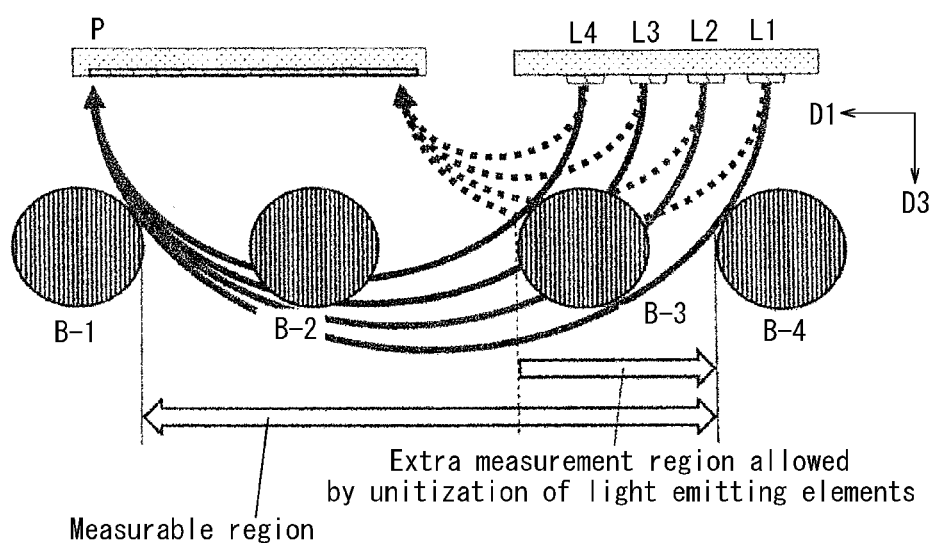
FIGS. 9A and 9B are diagrams illustrating a measurement mechanism of the sensor of the embodiment.
Figure 9B:
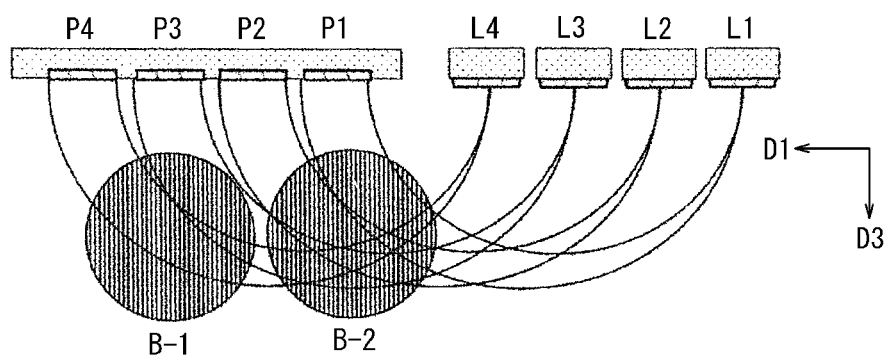

FIGS. 9A and 9B are schematic diagrams illustrating an effect of using the light emitting element unit 10 and an effect of using the light emitting element unit 10 and the photodetector element unit 20.

As illustrated in FIGS. 9A and 9B, in the sensor 100 a plurality of light emitting elements L1 to L4 and a plurality of photodetector elements P1 to P4 are arranged in the first direction D1 crossing the blood vessel B.

As illustrated in FIG. 9A, first, since the first direction D1 in which the plurality of light emitting elements L1 to L4 is arranged crosses the blood vessel B, the pulse wave signal may be obtained even when the relative position between the blood vessel B and the sensor 100 changes. In this example, the blood vessel B is displaced from a position B-1 to a position B4. As illustrated in FIG. 9A, the pulse wave signal may not be obtained when the blood vessel B is either in the position B-1 or the position B-4 but may be obtained when the blood vessel B is between the positions B-1 and B-4. That is, the sensor 100 of the present embodiment has an allowance for a measurable range. Therefore, even when the sensor 100 is displaced from an original position due to a movement of a person, or even when the blood vessel B moves within the human body, the sensor 100 may obtain the pulse wave signal stably and accurately.

Here, when one photodetector element has a large area and the light emitting element L is arranged at a long distance from the photodetector element and has increased emission intensity, the pulse wave signal may be obtained even when the relative position between the blood vessel B and the sensor 100 is changed. In this figure, providing the light emitting element L1 alone and increasing the emission intensity thereof may also substantialize a measurable range similar to that with the light emitting element unit configured with the light emitting elements.

In the sensor 100, as illustrated in FIG. 9B, the light emitted by the plurality of light emitting elements L1 to L4 is respectively received by the photodetector elements P1 to P4 arranged substantially parallel to the first direction D1 in which the plurality of light emitting elements L1 to L4 are arranged. Here, when a combination of the light emitting element L and the photodetector element P corresponding to each other is predetermined, a plurality of combinations of the light emitting elements L and the photodetector elements P with similar distances therebetween may be obtained. Therefore, when each of the light emitting elements L has the same emission intensity regardless of the distance from the photodetector element P, the pulse wave signal may be obtained by appropriately selecting the combinations of the light emitting elements L and the photodetector elements P, even when the relative position between the blood vessel B and the sensor 100 changes. Accordingly, the sensor 100 may enable low-voltage driving and facilitate control over the measurement.

Further, since in the sensor 100 the light emitting element unit 10 and the photodetector element unit 20 are linearly arranged in the first direction D1, in the first direction D1 the light emitting elements L and the photodetector elements P may form a long line and thus effectively increase the allowance of the measurable range to handle the change in the relative position between the sensor 100 and the blood vessel B in the first direction DE Also, this arrangement may shorten the distance between the light emitting elements L and the photodetector elements P, enabling prompt collection of information on the blood vessel upon driving the light emitting elements L. Accordingly, response performance of the sensor 100 may be enhanced.

Sensor 100A

Referring to FIG. 10, next, a sensor 100A according to another embodiment will be described.

The sensor 100A according to the another embodiment includes the light emitting element unit 10 and the photodetector element unit 20 in which a plurality of light emitting elements L or a plurality of photodetector elements P are arranged at center-to-center distances of at least 2 mm Arrangement in this manner allows, when the plurality of light emitting elements L are lit up, the plurality of photodetector elements P include a photodetector element Px for receiving the light having passed through the ulnar artery or the radial artery and a photodetector element Py for receiving the light having passed through neither the ulnar artery nor the radial artery. Here, a condition of the respective center-to-center distances of the plurality of light emitting elements L and the plurality of photodetector elements P differs depending on the artery to be measured. In this example, since the ulnar artery or the radial artery is measured, the center-to-center distance is 2 mm. The center-to-center distance between the light emitting element L1 and the photodetector element P3 and the center-to-center distance between the light emitting element L1 and the photodetector element P4 are both at least 2 mm.

Referring to FIG. 10, now, an effect of unitizing the photodetector elements P in the sensor 100A will be described.

Figure 10A:
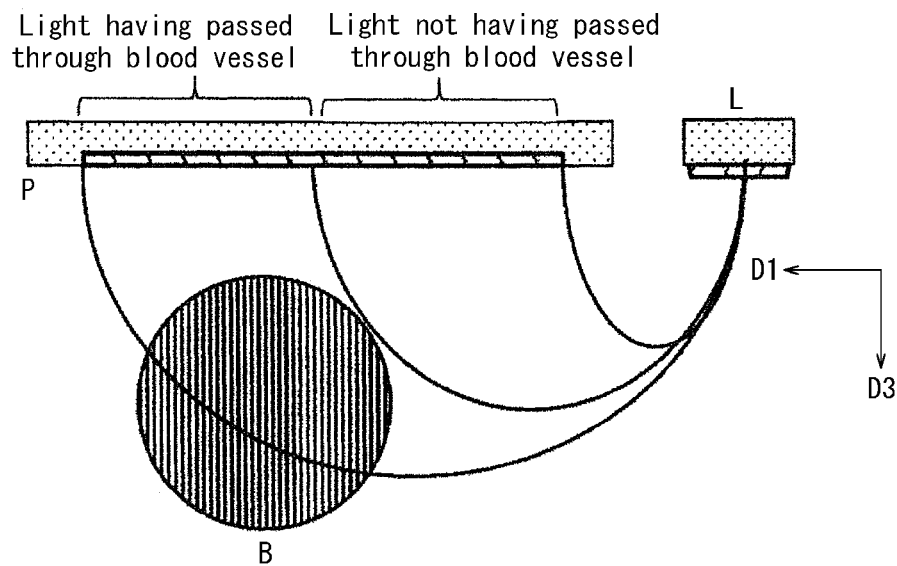
FIGS. 10A and 10B are diagrams illustrating the measurement mechanism of the sensor of the embodiment.
Figure 10B:
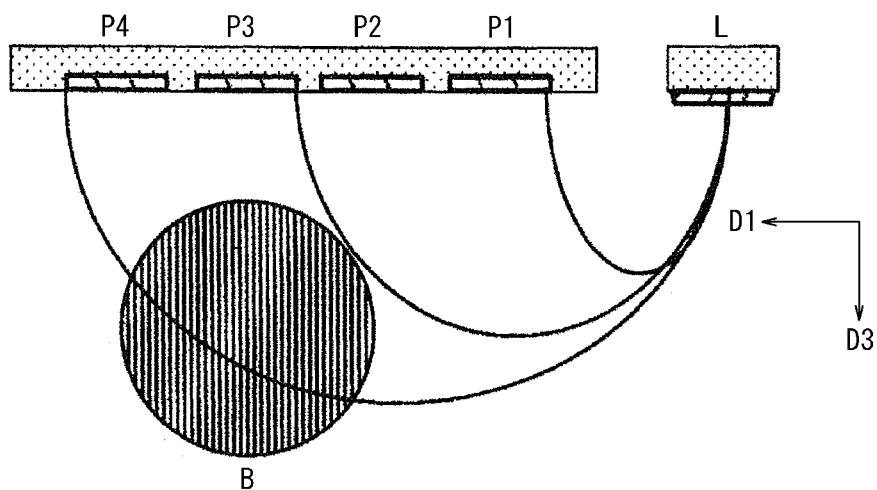

As illustrated in FIGS. 10A and 10B, one photodetector element with a large area for receiving the light obtains summarized information on the path of the light from the light emitting elements L to the photodetector element. On the other hand, a plurality of photodetector elements P may separately receive the light having passed through the blood vessel B and the light not having passed through the blood vessel B. In FIG. 10B, the photodetector elements P3 and P4 receive the light having passed through the blood vessel, while the photodetector elements P1 and P2 receive the light not having passed through the blood vessel. Therefore, selecting the photodetector element P having received the light containing the greatest quantity of information on the blood vessel B may enhance detection sensitivity of the sensor 100A. In an example of FIGS. 10A and 10B, appropriate selection may be made by selecting the photodetector element P4 by taking into account that the photodetector element P4 generates the detection signal with more information, or by combining the detection signals of the photodetector elements P3 and P4.

Further, the sensor 100A may use, in addition to the information on the light which has passed through the blood vessel B and then received by the photodetector element Px, information on the light which has not passed through the blood vessel B and then received by the photodetector element Py. In the sensor 100, based on the emission intensity of the light emitting element L and a depth of a position of the blood vessel B, an optimum distance between the light emitting element L for emitting the light which will contain more information on the blood vessel B and the photodetector element P is obtained. With respect to the sensor 100, a focus is placed on that the sensor 100 may have a plurality of combinations of the light emitting elements L and the photodetector elements P with the optimum distance therebetween. With respect to the sensor 100, that is, a focus is placed on uniform distances between the light emitting elements L and the photodetector elements P. With respect to the sensor 100A, on the other hand, a focus is placed on that the sensor 100A may also have a plurality of combinations of the light emitting elements L and the photodetector elements P with different distances therebetween.

A process performed on the detection signal as described above may include steps as follows:
(1) a data obtaining step of obtaining the detection signal generated by each of a plurality of photodetector elements P when a plurality of light emitting elements L are lit up;
(2) a data determination step of classifying a plurality of detection signals obtained at the data obtaining step into a first detection signal having periodic variations and a second detection signal having no periodic variations; and
(3) a data correction step of using a signal classified into the second detection signal at the data determination step for baseline correction of a signal classified into the first detection signal.

The following is a more detailed description of each of the above steps.

At the data obtaining step, the light emitting elements L are lit up, and detection signals corresponding to respective amounts of the light received by the plurality of photodetector elements P1 to P4 are obtained. Here, the plurality of light emitting elements L may be lit up concurrently or in sequence, or an optimum light emitting element L alone may be lit up. The optimum light emitting element L may be selected by, prior to the data obtaining step, inferring the position of the blood vessel B by separately lighting up each light emitting element L and receiving the light with each of the plurality of photodetector elements P.

At the data determination step, a plurality of detection signals obtained at the data obtaining step are classified into the first detection signal and the second detection signal. The first detection signal contains periodic variations of the amount of received light based on changes in the diameter of the blood vessel. More specifically, the first detection signal is indicative of an increase or a decrease in the amount of the received light in conjunction with the pulse. The determination may be made by checking the change in the amount of the received light in synchronization with the pulse or by checking whether autocorrelation is at equal to or over a certain value as compared to a reference waveform of the pulse. Here, the periodic variations of the first detection signal is not limited to variations continuously occurring at the same intervals, in consideration of an influence by arrhythmias and the like. In such a case, it is checked whether there is a recurring shape of a waveform (a track) of the detection signal corresponding to the increase or decrease in the amount of the received light caused by one pulsation. Here, the recurring shape of the detection signal corresponding to the increase or decrease in the amount of the received light does not need to be identical to a base shape but may be similar thereto. Also, such a shape of the detection signal may maintain a relationship of medical features alone.

On the other hand, the second detection signal does not have periodic variations of the signal corresponding to the amount of the received light. More specifically, the second detection signal does not include the recurring shape as seen in the first detection signal. The determination may be made based on whether a variation of a value and the pulse are correlated to each other or whether autocorrelation is under the certain value as compared to the reference waveform of the pulse. For example, when the detection signal is collected after inferring the position of the blood vessel B, the detection signal of the photodetector element Px may be classified into the first detection signal, and the detection signal of the photodetector element Py may be classified into the second detection signal.

At the data correction step, the signal classified into the first detection signal at the data determination step is corrected using the second detection signal. That is, the first detection signal is corrected by removing a background therefrom based on the second detection signal. The first detection signal includes recurring intensity variations in conjunction with the pulse in the shape of large waves caused by a movement and the like of the subject. Although having no specific variations of the signal strength in conjunction with the pulse, the second detection signal includes variations of the signal strength in the shape of large waves caused by a movement and the like of the subject. Therefore, the variation of the background of the first detection signal caused by a movement and the like of the subject is removed based on the second detection signal and thus cancelled. More specifically, in such a manner as to meet a background level of the first detection signal, a signal obtained by multiplying the second detection signal by a correction coefficient is subtracted from the first detection signal, and thus the pulse wave signal is obtained. The background level of the first detection signal may be obtained between the base shapes.

Performing the correction as described above enables an obtainment of a pulse wave signal highly reliable with less disturbance elements such as a movement of the human body. Therefore, using such a signal may enhance the reliability of the sensor.

Sensor Device 200

Figure 11:
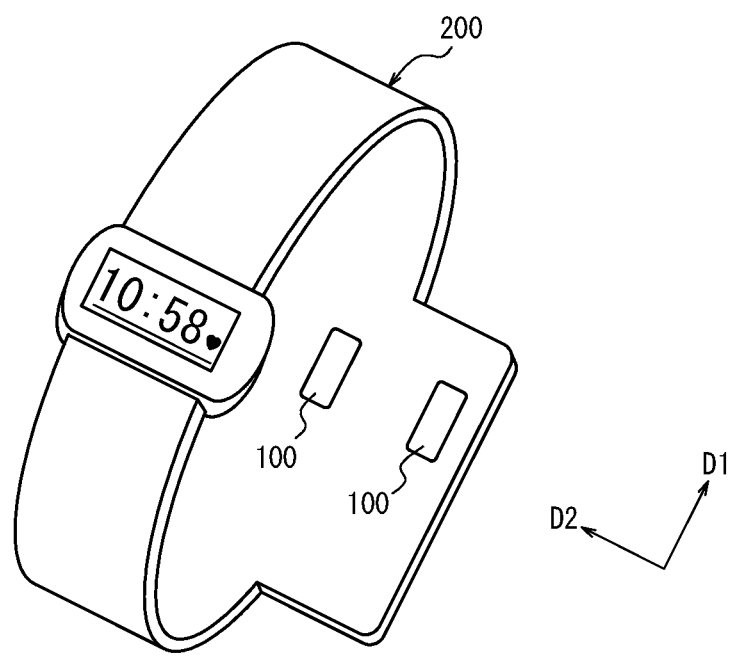
FIG. 11 is a perspective view of a sensor device according to the embodiment.

Next, a sensor device 200 using the sensor as described above will be described with reference to FIG. 11.

For example, the sensor 100 described above enables that the light is emitted by the light emitting element L to the surface of the living body of the subject, received by the photodetector element P after passing through the living body of the subject, and then detected as the pulse wave signal indicative of the change in the blood vessel such as the ulnar artery and the radial artery inside the living body. The sensor device 200 includes a pair of sensors 100 having the light emitting element or the photodetector element mounted thereon. The pair of sensors 100 have respective longitudinal sides extending along the first direction D1 and are arranged spaced apart from each other by a predetermined distance, e.g., 15 mm in the second direction D2. This arrangement allows the light emitting element L and the photodetector element P to be disposed substantially orthogonal to the ulnar artery in the wrist of the subject and also to measure the pulse wave at two positions spaced apart from each other by the predetermined distance, e.g., 15 mm.

The sensor device 200 of the present embodiment includes the light emitting element L for emitting the light to a test site, the photodetector element P for receiving at least one of the reflected light and the scattered light from the test site, and the circuit board 30 having at least one of the light emitting element L and the photodetector element P mounted thereon. In the sensor device 200, the light emitting surface of the light emitting element L is facing the circuit board 30.

The sensor device 200 of the present embodiment may obtain a pulse wave propagation velocity from a result of measurement of the pulse wave at two positions. Also, based on the pulse wave propagation velocity obtained in this manner, the sensor device 200 may, for example, calculate bio-information such as a blood pressure and estimate vascular age. For example, the following formula may be used to calculate the blood pressure (BP) from the pulse wave propagation velocity (PWV) with a and b serving as coefficients determined depending on the subject.

[Formula 1]

$$BP = a \times PWV + b \qquad (1)$$

The sensor device 200 of the present embodiment may continuously acquire a sensor signal such as the pulse wave. The sensor device 200 of the present embodiment may include a memory for storing the sensor signal obtained and various information, a controller for controlling an operation of the sensor and processing of the various information, a power source, and a communication unit for exchanging information with another device. The aforementioned memory may be, for example, the semiconductor memory or a magnetic memory. Further, the aforementioned controller may be a dedicated microprocessor or a general-purpose CPU for performing a specific function by reading a specific program.

Sensor System 1

Figure 12:
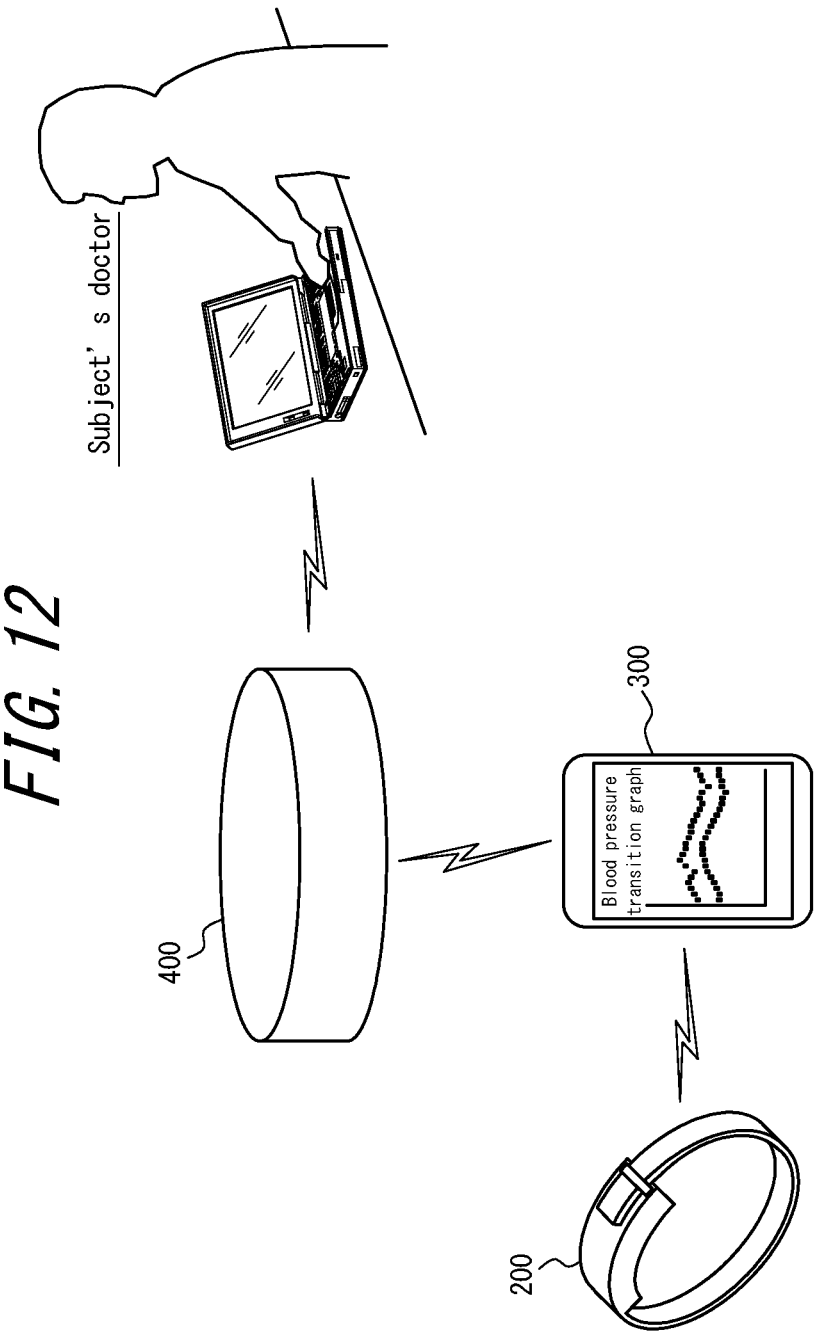
FIG. 12 is a diagram illustrating a schematic configuration of a sensor system according to the embodiment.

Next, a sensor system 1 which includes the sensor device 200 as described above will be described with reference to FIG. 12.

The sensor system 1 includes, in addition to the sensor device 200, a display apparatus 300 and a server 400.

The display apparatus 300 aggregates the sensor signals obtained by the sensor device 200 and performs various information processing on the sensor signals. The aggregation of the sensor signals is performed by receiving data from the sensor device 200 via a wired or wireless communication network. The display apparatus 300 displays the bio-information based on the sensor signals obtained by the sensor device 200 on the display. The display apparatus 300 also displays information processed by the server 400 on the display. The display apparatus 300 may be, for example, a dedicated terminal equipped with a display such as an LCD, or a general-purpose terminal such as a smart phone or a tablet PC.

The server 400 aggregates the bio-information of the subject transmitted from the display apparatus 300 and performs various information processing on the bio-information. The aggregation of the bio-information is performed by receiving data from the display apparatus 300 via the wired or wireless communication network. The server 400 transmits a result of the information processing based on the bio-information to the display apparatus 300. The server 400 may be an existing server which includes the memory such as the semiconductor memory and the controller such as the CPU.

In the sensor system 1, more specifically, the sensor signals obtained by the sensor device 200 are transmitted to the display apparatus 300 by the communication unit of the sensor device 200. Also, the bio-information obtained through the information processing performed on the sensor signals by the display apparatus 300 is transmitted to the server 400 by the communication unit of the display apparatus 300. When the server 400 receives the bio-information from the display apparatus 300, the controller of the server 400 performs various information processing based on the bio-information. For example, the server 400 may store, in the memory of the server 400, the bio-information received from the display apparatus 300 as data in chronological order together with reception time of the sensor signal. The controller of the server 400, for example, compares the data stored to past data of the same subject or data of another subject preliminarily stored in the memory of the server 400 and generates the best advice to the subject based on a result of the comparison. The communication unit of the server 400 transmits the data of the subject in chronological order and the generated advice to the display apparatus 300. The display apparatus 300 displays the data and the advice on a screen. The server 400, if necessary, may transmit the data in chronological order to, for example, a subject's doctor. Also, the server 400, if necessary, may receive an advice from the subject's doctor. Further, a functional unit for functioning similarly to the memory and the controller of the server 400 may be provided to the sensor device 200 or the display apparatus 300. In this case, the sensor system 1 does not necessarily need to include the server 400.

It is to be understood that the disclosure is not limited to the above embodiments but may be changed or modified various manners. For example, functions and the like included in each constituent, each step and the like may be rearranged without logical inconsistency, so as to combine a plurality of units or steps together or to divide them. For example, although in the present embodiment the pulse wave is measured by way of example, the disclosure is not limited thereto; the bio-information to be measured may be, for example, a blood flow rate, a heart rate, or the blood pressure. Also, the bio-information to be measured is not limited to one, but a plurality of bio-information may be measured by a combination of a plurality of sensors. For example, by combining a plurality of light emitting elements having different emission wavelengths, a plurality of different bio-information may be measured. For example, oxygen saturation of arterial blood may be obtained by using an infrared ray emitting diode and a near-infrared ray emitting diode.

REFERENCE SIGNS LIST 1 sensor system
10, 12 light emitting element unit
L light emitting element
20 photodetector element unit
P photodetector element
30 circuit board
32-36 light-transmitting portion
41-44, 51-55, 61-64 electrode 71, 72, 74 housing
81, 82 through-electrode
M optical path changing element
91, 93, 94, 96, 97, 99 electrode
92, 98 solder
95 wiring
100, 110, 120 sensor
200 sensor device
300 display apparatus
400 server

The invention claimed is:

1. A sensor comprising:
a light emitting element;
a photodetector element for receiving light emitted by the light emitting element; and
a circuit board having the light emitting element and the photodetector element mounted thereon, wherein a light emitting surface of the light emitting element is facing the circuit board provided with a light-transmitting portion for transmitting the light emitted by the light emitting element, and wherein the circuit board includes a portion for shielding the light emitted by the light emitting element, the portion penetrating through the circuit board from a position external to one surface of the circuit board to another position external to an opposite surface of the circuit board, and the portion not overlapping with the circuit board in a thickness direction of the circuit board.

2. The sensor according to claim 1, wherein a light receiving surface of the photodetector element is facing the circuit board provided with a light-transmitting portion for transmitting light to be received by the photodetector element.

3. The sensor according to claim 1, wherein the light-transmitting portion is provided with an optical path changing element for changing at least one of an optical path of the light emitted by the light emitting element and an optical path of the light to be received by the photodetector element.

4. The sensor according to claim 3, wherein the optical path changing element is any one of a spherical lens, an aspherical lens, a Fresnel lens, a cylindrical lens, and a prism.

5. The sensor according to claim 3, wherein the optical path changing element is configured to direct at least a portion of the light emitted by the light emitting element toward the photodetector element.

6. The sensor according to claim 1, wherein the circuit board comprises a resin comprising the light-transmitting portion.

7. The sensor according to claim 3, wherein the circuit board and the optical path changing element are integrally formed.

8. The sensor according to claim 1, wherein the light emitting element is configured with a plurality of light emitting elements linearly arranged.

9. The sensor according to claim 1, wherein the photodetector element is configured with a plurality of photodetector elements linearly arranged.

10. The sensor according to claim 1, wherein the light emitting elements are arranged on both sides of the photodetector element.

11. A sensor device comprising:
a light emitting element for emitting light to a test site;
a photodetector element for receiving at least one of reflection light and scattered light from the test site; and
a circuit board having at least one of the light emitting element and the photodetector element mounted thereon, wherein a light emitting surface of the light emitting element is facing the circuit board, and wherein the circuit board includes a portion for shielding the light emitted by the light emitting element, the portion penetrating through the circuit board from a position external to one surface of the circuit board to another position external to an opposite surface of the circuit board, and the portion not overlapping with the circuit board in a thickness direction of the circuit board.

12. A sensor system comprising:
a sensor device including a light emitting element for emitting light to a test site, a photodetector element for receiving at least one of reflection light and scattered light from the test site, and a circuit board having at least one of the light emitting element and the photodetector element mounted thereon, wherein a light emitting surface of the light emitting element is facing the circuit board, and wherein the circuit board includes a portion for shielding the light emitted by the light emitting element, the portion penetrating through the circuit board from a position external to one surface of the circuit board to another position external to an opposite surface of the circuit board, and the portion not overlapping with the circuit board in a thickness direction of the circuit board; and
a display apparatus for displaying bio-information based on a sensor signal acquired by the sensor device.

13. The sensor according to claim 1, wherein the circuit board is formed of a deformable material.

14. The sensor according to claim 1, further comprising:
a housing which houses the light emitting element; and
wherein the portion extends into the housing.

15. The sensor device according to claim 11, further comprising:
a housing which houses the light emitting element; and
wherein the portion extends into the housing.

16. The sensor system according to claim 12, further comprising:
a housing which houses the light emitting element; and
wherein the portion extends into the housing.

* * * * *